US010504614B2

(12) United States Patent
Grgicak et al.

(10) Patent No.: US 10,504,614 B2
(45) Date of Patent: Dec. 10, 2019

(54) SYSTEMS AND METHODS FOR DETERMINING AN UNKNOWN CHARACTERISTIC OF A SAMPLE

(71) Applicants: Rutgers, The State University of New Jersey, New Brunswick, NJ (US); Trustees of Boston University, Boston, MA (US); Massachusetts Institute of Technology, Cambridge, MA (US)

(72) Inventors: Catherine M. Grgicak, Boston, MA (US); Desmond S. Lun, Philadelphia, PA (US); Muriel Medard, Belmont, MA (US); Harish Swaminathan, Philadelphia, PA (US)

(73) Assignees: RUTGERS, THE STATE UNIVERSITY OF NEW JERSEY, New Brunswick, NJ (US); TRUSTEES OF BOSTON UNIVERSITY, Boston, MA (US); MASSACHUSETTS INSTITUTE OF TECHNOLOGY, Cambridge, MA (US)

( * ) Notice: Subject to any disclaimer, the term of this patent is extended or adjusted under 35 U.S.C. 154(b) by 489 days.

(21) Appl. No.: 15/027,868

(22) PCT Filed: Oct. 7, 2014

(86) PCT No.: PCT/US2014/059503
§ 371 (c)(1),
(2) Date: Apr. 7, 2016

(87) PCT Pub. No.: WO2015/054259
PCT Pub. Date: Apr. 16, 2015

(65) Prior Publication Data
US 2016/0239606 A1    Aug. 18, 2016

Related U.S. Application Data

(60) Provisional application No. 62/055,446, filed on Sep. 25, 2014, provisional application No. 61/887,831, filed on Oct. 7, 2013.

(51) Int. Cl.
| | |
|---|---|
| *G01N 33/48* | (2006.01) |
| *G01N 33/50* | (2006.01) |
| *G16B 40/00* | (2019.01) |
| *C12Q 1/6851* | (2018.01) |
| *C12Q 1/686* | (2018.01) |

(52) U.S. Cl.
CPC ............. *G16B 40/00* (2019.02); *C12Q 1/686* (2013.01); *C12Q 1/6851* (2013.01)

(58) Field of Classification Search
None
See application file for complete search history.

(56) References Cited

U.S. PATENT DOCUMENTS

| 2002/0152035 A1 | 10/2002 | Perkin |
| 2009/0155891 A1 | 6/2009 | Tamaoki et al. |
| 2010/0021885 A1* | 1/2010 | Fielden ................ C12Q 1/6876 435/6.13 |
| 2012/0237939 A1 | 9/2012 | Reed et al. |

\* cited by examiner

*Primary Examiner* — Russell S Negin
(74) *Attorney, Agent, or Firm* — Fox Rothschild LLP

(57) ABSTRACT

Computerized analysis methods and systems to implement the computerized analysis methods are disclosed herein. Specifically, the present disclosure relates to systems and methods for determining an unknown characteristic of a sample.

21 Claims, 11 Drawing Sheets

| Injection time (s) | DNA amount (ng) | Number of samples | Injection time (s) | DNA amount (ng) | Number of samples | Injection time (s) | DNA amount (ng) | Number of samples |
|---|---|---|---|---|---|---|---|---|
| 5 | 0.016 | 4 | 10 | 0.016 | 4 | 20 | 0.016 | 4 |
|  | 0.031 | 4 |  | 0.031 | 4 |  | 0.031 | 4 |
|  | 0.047 | 4 |  | 0.047 | 4 |  | 0.047 | 4 |
|  | 0.063 | 4 |  | 0.063 | 4 |  | 0.063 | 4 |
|  | 0.125 | 4 |  | 0.125 | 4 |  | 0.125 | 4 |
|  | Total | 20 |  | Total | 20 |  | Total | 20 |

| Injection time (s) | DNA amount (ng) | Number of samples | Injection time (s) | DNA amount (ng) | Number of samples | Injection time (s) | DNA amount (ng) | Number of samples |
|---|---|---|---|---|---|---|---|---|
| 5 | 0.031 | 2 | 10 | 0.031 | 2 | 20 | 0.031 | 2 |
|  | 0.047 | 4 |  | 0.047 | 4 |  | 0.047 | 4 |
|  | 0.063 | 6 |  | 0.063 | 6 |  | 0.063 | 6 |
|  | 0.125 | 8 |  | 0.125 | 8 |  | 0.125 | 7 |
|  | 0.25 | 10 |  | 0.25 | 10 |  | 0.25 | 10 |
|  | Total | 30 |  | Total | 30 |  | Total | 29 |

| Injection time (s) | DNA amount (ng) | Number of samples | Injection time (s) | DNA amount (ng) | Number of samples | Injection time (s) | DNA amount (ng) | Number of samples |
|---|---|---|---|---|---|---|---|---|
| 5 | 0.047 | 1 | 10 | 0.047 | 1 | 20 | 0.047 | 1 |
|  | 0.063 | 3 |  | 0.063 | 3 |  | 0.063 | 3 |
|  | 0.125 | 5 |  | 0.125 | 5 |  | 0.125 | 5 |
|  | 0.25 | 7 |  | 0.25 | 7 |  | 0.25 | 7 |
|  | Total | 16 |  | Total | 16 |  | Total | 16 |

| Injection time (s) | DNA amount (ng) | Number of samples | Injection time (s) | DNA amount (ng) | Number of samples | Injection time (s) | DNA amount (ng) | Number of samples |
|---|---|---|---|---|---|---|---|---|
| 5 | 0.063 | 2 | 10 | 0.063 | 2 | 20 | 0.063 | 2 |
|  | 0.125 | 5 |  | 0.125 | 5 |  | 0.125 | 5 |
|  | 0.25 | 6 |  | 0.25 | 6 |  | 0.25 | 6 |
|  | Total | 13 |  | Total | 13 |  | Total | 13 |

| Injection time (s) | DNA amount (ng) | Number of samples | Injection time (s) | DNA amount (ng) | Number of samples | Injection time (s) | DNA amount (ng) | Number of samples |
|---|---|---|---|---|---|---|---|---|
| 5 | 0.0625 | 1 | 10 | 0.0625 | 1 | 20 | 0.0625 | 1 |
|  | 0.125 | 5 |  | 0.125 | 5 |  | 0.125 | 5 |
|  | 0.25 | 8 |  | 0.25 | 8 |  | 0.25 | 8 |
|  | Total | 14 |  | Total | 14 |  | Total | 14 |

FIG. 5

| Variable | Model description | Distribution of the variable |
|---|---|---|
| Dropout rate of alleles ($\alpha$) | Exponentially decreasing curve | $\alpha = ae^{bx}$, where $x$ is the DNA mass from the contributor with the allele |
| Rate of non-occurrence of stutter ($\beta$) | Exponentially decreasing curve | $\beta = ae^{bx}$, where $x$ is the DNA mass in the parent allele that gives rise to stutter |
| Mean of true peak heights ($\mu_t$) | Line with a positive slope | $\mu_t = ax + b$, where $x$ is the DNA mass in the true peak |
| Standard deviation of true peak heights ($\sigma_t$) | Line with a positive slope | $\sigma_t = ax + b$, where $x$ is the DNA mass in the true peak |
| Mean of noise peak heights ($\mu_n$) | Line with a positive slope | $\mu_n = ax + b$, where $x$ is the DNA mass that the sample was amplified with |
| Standard deviation of noise peak heights ($\sigma_n$) | Line with a positive slope | $\sigma_n = ax + b$, where $x$ is the DNA mass that the sample was amplified with |
| Mean of stutter ratios ($\mu_s$) | Exponentially decreasing curve | $\mu_s = ae^{bx} + c$, where $x$ is the DNA mass in the parent allele that gives rise to stutter |
| Standard deviation of stutter ratios ($\sigma_s$) | Exponentially decreasing curve | $\sigma_s = ae^{bx} + c$, where $x$ is the DNA mass in the parent allele that gives rise to stutter |

FIG. 11

SYSTEMS AND METHODS FOR DETERMINING AN UNKNOWN CHARACTERISTIC OF A SAMPLE

CROSS-REFERENCE TO RELATED APPLICATIONS

This application is the U.S. National Phase of International Patent Application Serial No. PCT/US2014/059503 filed Oct. 7, 2014 which claims the benefit of priority under 35 U.S.C. § 119(e) of U.S. Provisional Application No. 62/055,446 filed Sep. 25, 2014 and U.S. Provisional Application No. 61/887,831 filed Oct. 7, 2013, the disclosures of which are hereby incorporated by reference in their entireties.

STATEMENT REGARDING FEDERALLY SPONSORED RESEARCH

This invention was made with government support under Grant No. 2011-DN-BX-K558 awarded by National Institute of Justice, Grant No. 2012-DN-BX-K050 awarded by the National Institute of Justice, and under Grant No. DBI-1126052 by the National Science Foundation. Accordingly, the Government has certain rights in this invention.

FIELD OF THE DISCLOSURE

The present disclosure relates to computerized analysis methods and systems to implement the computerized analysis methods. Specifically, the present disclosure relates to systems and methods for determining an unknown characteristic of a sample.

BACKGROUND OF THE INVENTION

Short Tandem Repeats, or STRs, are repetitive sequences 1-7 base pairs in length that are scattered throughout the human genome. One of the commonly used applications of STRs is in the field of human identification for forensic purposes. An STR DNA profile developed from a biological sample collected at a crime scene is compared with that of a person of interest or run against a database to check for a match. Biological evidence obtained at crime scenes is used to create a DNA profile and compared with the profile of a suspect to check whether a match occurs. In some instances, multiple people might have contributed to the evidence, giving rise to mixtures. The true number of contributors to a biological sample is never known with certainty. The DNA analyst is required to make assumptions about the number of contributors to the sample in order to reach a conclusion as to whether the suspect should be excluded or included as a potential contributor to the sample.

The Scientific Working Group on DNA Analysis Methods (SWGDAM) recommends that forensic reports include a statement as to the assumption made about the number, or the minimum number of contributors, to the sample being investigated. The number of contributors to a crime scene sample is generally unknown and must be estimated by the analyst based on the electropherogram obtained. The assumption on the number of contributors affects statistics used to assess the weight of DNA evidence, e.g., the Likelihood Ratio. Thus, it is useful to have a good estimate on the number of contributors to the sample.

Two commonly used methods to provide statistical weight for the inclusion of a person as a contributor are the Likelihood Ratio (LR) method and the Random Man Not Excluded (RMNE) method. Both of these methods require assumptions to be made concerning the number of contributors. Different assumptions lead to vastly different values for the LR method or different conclusions (i.e., inclusion or exclusion) in the case of the RMNE method. The most widely used method currently is Maximum Allele Count (MAC). This method seeks to identify the minimum number of individuals who could have contributed to a sample by counting the number of alleles observed at each locus, taking the maximum value over all the loci and dividing it by two.

Though methods to infer the number of contributors to a forensic sample exist, there are issues associated with all of them. Stochastic effects associated with DNA extraction, the PCR process and pipetting lead to non-detection of alleles (dropout). Further, allele sharing and PCR amplification artifacts like stutter occur frequently and make it difficult to interpret low-template, mixture profiles. These make it difficult to accurately estimate the number of contributors to a sample. The MAC method does not work well with complex mixtures because of sharing of alleles between the contributors. Guidelines have been established for estimating the number of contributors for high and low template samples using the total number of alleles observed. This method is prone to misclassification due to extensive allele sharing, dropout and stutter. Methods that do not rely only upon the number of alleles observed but also use the frequencies of the alleles in the signal have been created. For example, one method employing a Bayesian network has been developed and utilizes a probabilistic approach to infer the number of contributors to forensic samples. This method has been shown to work better than MAC with degraded DNA and with higher number of contributors. A Maximum Likelihood Estimator (MLE) method has also shown to give more accurate results than MAC with higher number of contributors and degraded DNA. A Probabilistic Mixture Model can infer the number of contributors to a sample based on the frequencies of the alleles observed.

SUMMARY OF THE INVENTION

A method and system is disclosed that takes a profile of an unknown sample as input, along with an amount of the sample, a set of calibration data, and a set of experimental conditions to determine an unknown characteristic of the unknown sample. The method and system then returns likelihoods for the number of contributors to the sample. This method and system uses quantitative data (e.g., peak heights in the signal) to estimate the number of contributors. In addition, it also uses the frequencies of the alleles observed. The method and system also incorporates stutter in its calculation. Probability of dropout is used in the calculation, as well as the various possible mixture ratios.

BRIEF DESCRIPTION OF THE DRAWINGS

Embodiments will be described with reference to the following drawing figures, in which like numerals represent like items throughout the figures, and in which:

FIG. 5 represents the 1-, 2-, 3-, 4- and 5-person experimental samples comprising Testing Set 1.

FIG. 11 shows the variables used in example 1 and the distribution used to model them as a function of DNA mass.

DETAILED DESCRIPTION OF THE INVENTION

Figure 1:
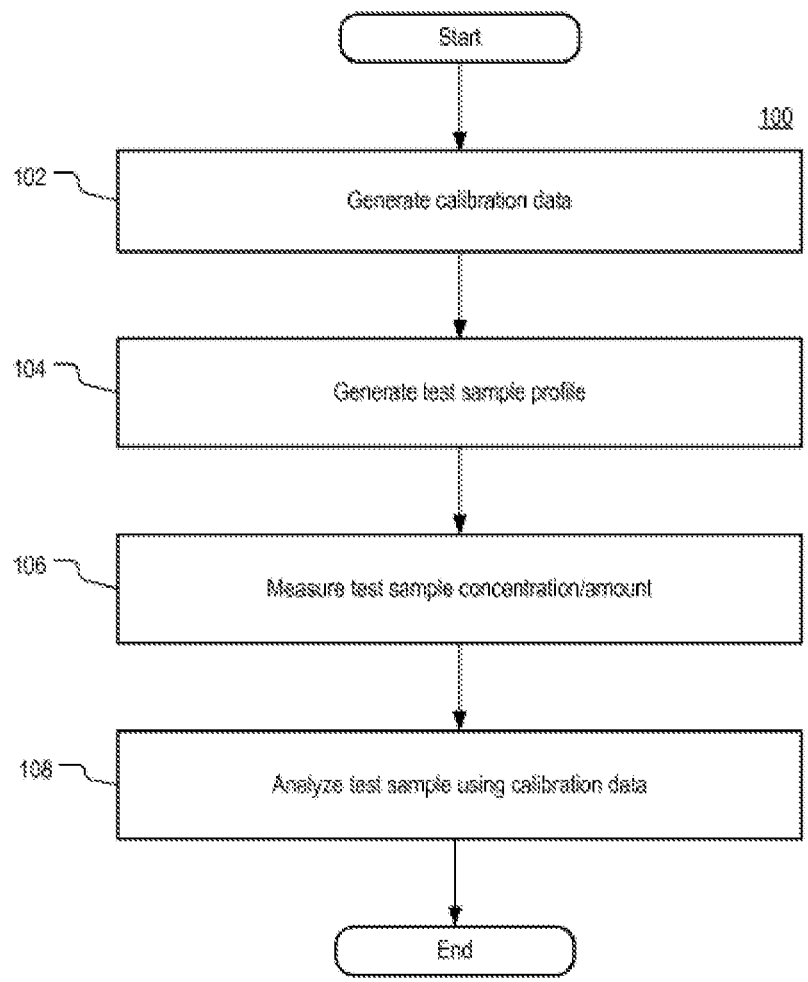
FIG. 1 is a flow chart that is useful for understanding method for determining an unknown characteristic of a sample.

Conventional methods used to infer the number of contributors to a forensic sample use qualitative data, i.e. the frequencies of the alleles observed in the sample, but do not use the quantitative data obtained, i.e. the heights of the peaks in the signal. The height of a peak is a good indicator of the number of alleles that gave rise to a peak. This is information that could be used in estimating the number of individuals that gave rise to the sample. In addition, these conventional methods are not suitable for low template mixtures, which exhibit high levels of dropout (loss of signal) and elevated stutter (a frequently-occurring artifact that often results in an additional peak one repeat unit less or one repeat more than the allele).

The present invention solves these problems by calculating the a posteriori probability (APP) on the number of contributors to a DNA sample. In addition to using the qualitative information contained in the signal, i.e. the allele frequencies, the present invention also makes use of the quantitative information present, i.e. the heights of the peaks. The heights of the peaks increase with an increase in the amount of input DNA and are an indicator of the mixture ratio and the number of copies of an allele that gave rise to a peak. This is information is useful in estimating the number of individuals that gave rise to a sample. In addition, the present invention accounts for the dropout of alleles and the formation of stutter peaks.

A. Overview

Methods and systems are disclosed to estimate the number of contributors to a forensic DNA sample. These methods and systems are designed to aid DNA analysts in mixture interpretation by computing likelihoods for the number of contributors to the sample. Although described in reference to a DNA application, the methods and systems disclosed herein are applicable to any analytical application where one seeks to determine the number of constituents in a mixture. Non-limiting examples include the number of crystallites in a complex Powder X-ray Diffraction mixture, the number of elements in an energy dispersive x-ray spectrograph, the number of molecules in nuclear magnetic resonance spectra, the number of elements in photoelectron spectroscopy, and the number of redox couples in a cyclic voltammogram.

The methods and systems work by taking the profile of an unknown evidence sample as input, along with an amount of DNA that has been amplified, and the allele frequency table to be used. The methods and systems then return likelihoods for the number of contributors to the sample. The methods and systems are the first tool of its kind that uses quantitative data (e.g., peak heights in the signal) to estimate the number of contributors. In addition, the methods and systems also use the frequencies of the alleles observed. The methods disclosed herein are also the first methods that incorporates stutter in their calculations. In one example, reverse stutter, one repeat unit smaller than the allele, may be considered as the most common form of stutter. Probability of dropout is used in the calculations, as well as the various possible mixture ratios.

B. Calibration of the Method and System

The methods and systems use the quantitative information contained in the signal in the form of peak heights to calculate the probabilities for the number of contributors. This involves characterizing the dependence of variables such as probability of dropout, probability of stutter and true, stutter and baseline noise peak heights on the input DNA mass. This is done by using single source calibration samples with known genotypes obtained from samples amplified from a wide range of input DNA masses.

Calibration data for software used by the methods and systems may be obtained from single-source samples. For example, profiling results from different DNA contributors using different amounts of template DNA (e.g., ranging from 0.07 ng to 0.25 ng) may be used to calibrate the software. To calibrate, a probability density function (PDF) of the peak heights/areas (i.e. signal strength) in the signal may be created at each locus for every DNA amount. Additionally, a PDF of the stutter proportion (i.e. the signal ratio relative to the true peak), a PDF of the noise heights/areas, and a model for the drop-out rate may be created at each locus. This is accomplished by classifying each peak in the calibration data as one of a true peak (i.e., a peak arising out of an allele in the contributor); a stutter peak (i.e., a peak in the stutter position of a true peak); and a noise peak (i.e., any peak other than a true or a stutter peak) and by examining the number of undetected true peaks.

The PDFs indicate how likely it is to observe a peak of a particular height, given that the peak is either a true, stutter, or noise peak. Also indicated is the likelihood of allele drop-out. The heights of the peaks in all the three categories may be modeled using the normal distribution.

A Monte Carlo approach can be utilized to compute the likelihood for the number of contributors. Genotypes for the "n" contributors are picked based on the frequencies of the alleles in the frequency table. A mixture ratio is picked at random since all mixture ratios are assumed to occur with equal probability. Based on the evidence observed, the likelihood of observing the heights of the peaks given the contributor genotypes, the mixture ratio, the amount of DNA amplified is computed using the calibration data. This is repeated a certain number of times. The average of the values computed is the likelihood of observing the evidence, given "n" contributors. The "n" that results in the highest likelihood is taken to be the number of contributors most supported by the evidence as calculated by the disclosed system.

Referring now to FIG. 1, a flow chart is provided that shows an example process 100 for analyzing a test sample. The actions described in this process can be performed on well-known laboratory equipment, such as electrophoresis analyzers, connected to a general purpose computer running one or more specialized software packages that can be executed to perform the steps described. Calibration data is generated using the laboratory equipment that will be used to analyze the test sample 102.

Figure 2:
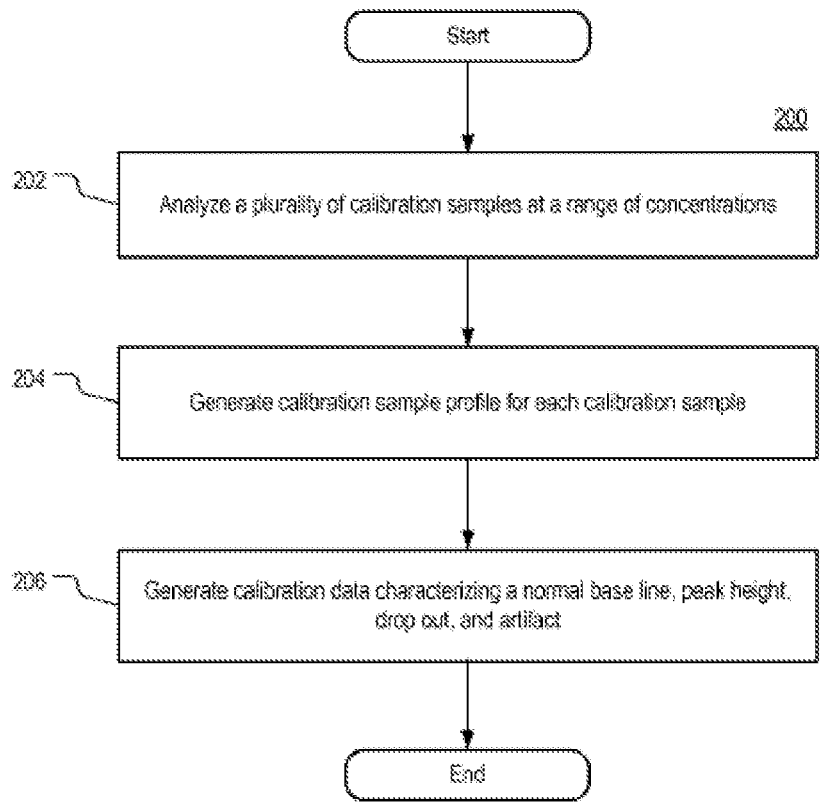
FIG. 2 is a flow chart that is useful for understanding a method for generating calibration data.

To generate the calibration data, a number of calibration samples are analyzed using the laboratory equipment using a process 200 illustrated in FIG. 2. All of the calibration samples are analyzed at a range of concentrations using the laboratory's standard operating procedures 202. Each calibration sample may correspond to a particular characteristic of the material analyzed. For example, when used to determine the number of contributors in a DNA sample, each calibration sample corresponds to a known single-source (i.e. a single contributor) DNA sample at a particular concentration that is obtained using the laboratory's standard operating procedure. For example, a large number of distinct DNA samples, such as fifty or more distinct DNA samples, may be used. Variation can be introduced by creating samples with a range of DNA concentrations. By increasing the ranges and number of combinations, the total number of samples analyzed can be 5-100 times more than the number of distinct DNA samples used.

A calibration sample profile is generated for each calibration sample analyzed 204. The calibration data is generated by aggregating the results from each calibration sample. The calibration samples are selected to provide a broad characterization of all practical variation in the sample material, the amount of sample and in laboratory process. The calibration data is generated that characterizes a baseline, peak height, drop out, and artifacts present in the calibration samples 206. As described above, the calibration samples correspond to a wide variation of samples and laboratory and experimental conditions. Utilizing the calibration data, the specialized software implementing the disclosed method can determine the likelihood an identified data point, given a mixture ratio, genotype and DNA amount is a true peak, a noise peak, or a stutter peak. This is because the calibration samples data takes into account the natural variation caused in the material itself and the variation introduced by the idiosyncrasies of the particular laboratory process used. Referring again to FIG. 1, a test sample profile is analyzed and generated using the same equipment and operating procedures that is used to analyze the calibration samples 104. Since an important function of the calibration data is to include variation introduced by the laboratory process, including the particular equipment used, it is important that the test sample be processed using the same equipment and procedures. The test sample is a sample of material where the characteristic of interest is unknown. In the example of forensic DNA analysis, the unknown characteristic may be the number of contributors to the DNA sample (i.e., the number of individuals whose DNA is included in the sample). The amount of the test sample is also measured 106.

Figure 3:
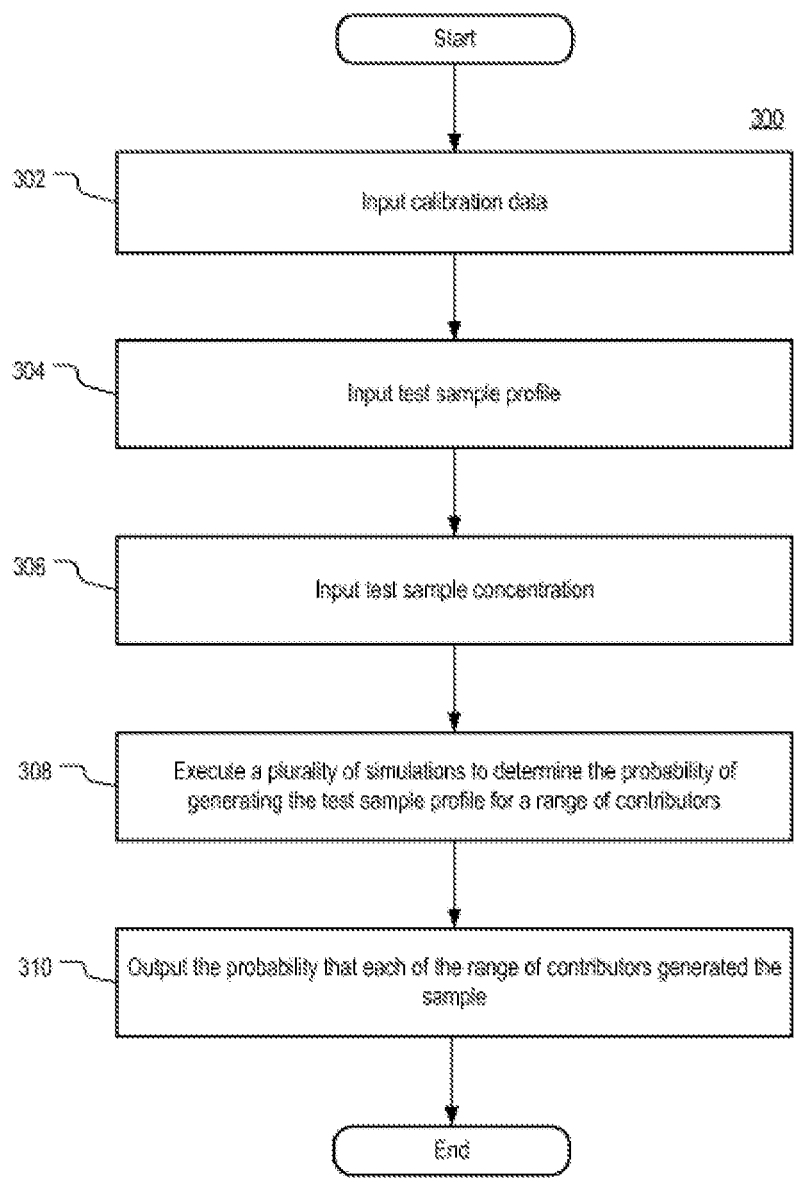
FIG. 3 is a flow chart that is useful for understanding a method for analyzing a sample using generated calibration data.

The test sample profile is then analyzed using the calibration data for a determination of the unknown characteristic 108. Referring now to FIG. 3, a process 300 for determining the unknown characteristic is shown. The calibration data 302, test sample profile 304, and sample amount/concentration 306 is input into one or more specialized software packages implementing the disclosed process. A number of simulations are executed by the software across a range of defined values for the undefined characteristic 308. In the example of contributors in a DNA sample, the simulations may be run multiple times for each number of possible contributors, for example, between one and five. After a suitable number of simulations, probabilities that the DNA sample came from each possible number of contributes converge on a final value. The probability that each number of possible contributors gave rise to the stain is generated and output. 310. Although described with respect to forensic DNA analysis, this method can be used in a number of different applications. For example, in chemical analysis, this method can be used to determine the number of constituents in an unknown sample. For example, powder x-ray diffraction of unknown sample (i.e. soil) which contains an unknown numbers crystallites, mass spectra of an unknown sample which contain unknown numbers of compounds, energy dispersive x-ray generated from a questioned sample that contain an unknown number of elements and nuclear magnetic spectra of samples which contain unknown numbers of compounds.

Figure 4:
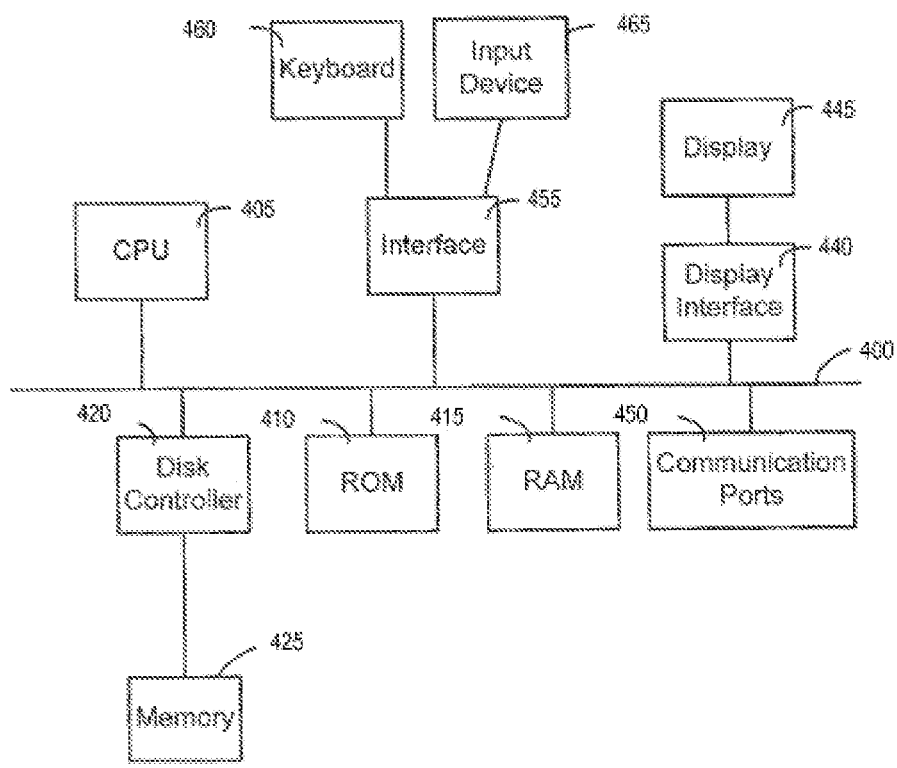
FIG. 4 is a block diagram that is useful for understanding exemplary computer hardware which is capable of implementing the methods described herein.

FIG. 4 depicts a block diagram of hardware that may be used to contain or implement program instructions to perform the methods described above. A bus 400 serves as an information highway interconnecting the other illustrated components of the hardware. CPU 405 is the central processing unit of the system, performing calculations and logic operations required to execute a program. CPU 405, alone or in conjunction with one or more of the other elements disclosed in FIG. 4, is an example of a production device, computing device or processor as such terms are used within this disclosure. Read only memory (ROM) 410 and random access memory (RAM) 415 constitute examples of non-transitory computer-readable storage media.

A controller 420 interfaces with one or more optional non-transitory computer-readable storage media 425 to the system bus 400. These storage media 425 may include, for example, an external or internal DVD drive, a CD ROM drive, a hard drive, flash memory, a USB drive or the like. As indicated previously, these various drives and controllers are optional devices.

Program instructions, software or interactive modules for providing the interface and performing any querying or analysis associated with one or more data sets may be stored in the ROM 410 and/or the RAM 415. Optionally, the program instructions may be stored on a tangible non-transitory computer-readable medium such as a compact disk, a digital disk, flash memory, a memory card, a USB drive, an optical disc storage medium, such as a Blu-Ray™ disc, and/or other recording medium.

An optional display interface 440 may permit information from the bus 400 to be displayed on the display 445 in audio, visual, graphic or alphanumeric format. Communication with external devices, such as a printing device, may occur using various communication ports 450. A communication port 450 may be attached to a communications network, such as the Internet or an intranet. Alternatively, such communications port 450 can be used to facilitate automated collection of data from suitable laboratory equipment. For example, the communication port 450 can be connected to an electrophoresis analyzer to facilitate collection of calibration data and/or actual test sample data. According to one aspect of the invention, the laboratory equipment can be under the direct control of the CPU for implementing one or more of the processing steps described herein.

The hardware may also include an interface 455 which allows for receipt of data from input devices such as a keyboard 460 or other input device 465 such as a mouse, a joystick, a touch screen, a remote control, a pointing device, a video input device and/or an audio input device.

It should be noted that one or more of processes 100, 200, and 300 may be executed by one or more processors that are part of a computer system. Furthermore, it should be noted that FIGS. 1-4 are provided as examples only. At least some of the steps in processes 100, 200, and 300 may be performed in a different order than represented, performed concurrently, or omitted.

C. Modeling of Variables

In order to compute the probability of observing the heights of the peaks in the signal, peak heights can be modeled using, for example, the Gaussian distribution, which is a simple distribution and is easy-to-use. The heights of the allelic peaks in the calibration samples may be tested for normality using, for example, the Kolmogorov-Smirnov (K-S) test. The K-S test is a test for the equality of continuous probability distributions that can be used to compare a sample with a reference probability distribution. In using a Gaussian distribution, if no significant difference is found between the Gaussian distribution and the distribution of the peak heights, then the Gaussian distribution is a good approximation of the distribution of the allele peak heights. Using this assumption then, for a given mass of DNA, true, noise and stutter peak heights are described using their respective mean and standard deviation. Other distributions may be used when appropriate.

The systems and methods herein account for the formation of stutter peaks, a PCR artifact that results in amplification of alleles extraneous to the ones originally present in the DNA sample. The systems and methods herein also account for the formation of reverse stutter (additional peaks in the n−4 position of alleles) as well as forward stutter (additional peaks in the n+4 position of alleles). Since the height of the stutter peak is dependent upon the height of the parent allele, modeling of the stutter peaks is done using the stutter ratio (r):

$$r = \frac{h_s}{h_a},$$

where $h_s$ is the height of the stutter peak and $h_a$ is the height of the allelic peak causing stutter.

With homozygous samples, it is not always possible to say with certainty whether both alleles have been amplified or whether one of the alleles has dropped out. Hence, at the AMEL locus, the sex determining locus, homozygous samples ('X', 'X') are used for calibration of noise peak heights and heterozygous samples ('X', 'Y') are used for calibration of allele peak heights. At all other loci, only the heterozygous samples are used for calibration of allele, noise and stutter peak heights. Dropout rates and rate of occurrence of stutter were also computed using only the heterozygous samples.

Samples are separated based on their time of injection. From the profiles obtained, observed peaks are separated into one of four categories: true peaks (peaks from alleles present in the contributor to the sample), reverse stutter peaks (peaks in the n−4 position of true peaks), forward stutter peaks (peaks in the n+4 position of true peaks) and noise peaks (all other peaks having alleles in the frequency table or in the n−4 or n+4 position of alleles in the frequency table). In each category, the parameters of the distribution, for example Gaussian distribution, (namely the mean and the standard deviation) are computed at the seven DNA amounts for each locus. Dropout rates and rate of occurrence of stutter are also computed at all the DNA amounts for each locus. In order to use the values from the calibration set, the various variables in the algorithm are modeled as a function of DNA mass.

D. Algorithm

The systems and methods herein calculate the a posteriori probability (APP) on the number of contributors N given a particular evidence sample (electrophoresis profile) E. That is, the systems and methods calculate Pr(N=n|E) for n=1, 2, 3, . . . . Using Baye's rule, the following formula is obtained:

$$Pr(N = n \mid E) = \frac{Pr(E \mid N = n)Pr(N = n)}{Pr(E)},$$

for n=1, . . . , $n_{max}$. An assumption is that a priori N is uniformly distributed between 1 and $n_{max}$, the maximum possible number of contributors. Since Pr(E) is the same for all n, the result is that:

$$Pr(N=n|E) \propto Pr(E|N=n).$$

The STR loci used for forensic DNA analysis are assumed to be in linkage equilibrium and independent of each other. L is the set of all loci in the evidence sample and $E_l$ is the evidence at locus l. The result is that:

$$Pr(E \mid N = n) = \prod_{l \in L} Pr(E_l \mid N = n).$$

$G_i$, $\Theta_i$ respectively represent the genotype and mixture proportion of contributor $i \in \{1, \ldots, n_{max}\}$. G and $\Theta$ respectively represent the $n_{max}$-component vectors of $G_i$ and $\Theta_i$. The result is:

$$Pr(E_l \mid N = n) = \int_{\theta \in \Delta^{n-1}} \sum_{g \in \mathcal{G}^n} Pr(E_l \mid G = g, \Theta = \theta, N = n) Pr(G = g) f_\Theta(\theta) \quad (1)$$

where $$\Delta^{n-1} = \left\{ (x_1, \ldots, x_n) \in \mathbb{R}^n \,\middle|\, \sum_{i=1}^n x_i = 1, x_i \geq 0 \,\forall\, i \right\}$$

is the unit n−1 simplex, $\mathcal{G}$ is the space of possible genotypes (for both alleles of a contributor) in the population, and $f_\Theta$ is the probability density function of $\Theta$, which is assumed to be uniform over $\Delta^{n-1}$. In (1), the integration is over all the mixture proportions and the sum is over all the different genotypes. The distribution $Pr(E_l|G=g, \Theta=\theta, N=n)$ can be estimated from the single source calibration samples with known genotypes.

The systems implement the methods using a Monte-Carlo sampling algorithm. At each locus, random samples of g and θ are generated using the allele frequencies in the background population and $f_\Theta$, respectively. No correlation is made between the genotypes of the various individuals or between the two alleles of one individual. The Amelogenin locus is different from the others since it is not based on STRs. Only two genotypes are possible at this locus: ('X', 'X') for females and ('X', 'Y') for males. At this locus, it is assumed that both the genotypes are equally likely to occur and generate genotypes for the n contributors.

For every allele in the genotype of all the contributors, dropout of the allele and the formation of reverse and forward stutter from that allele are simulated by a Bernoulli trial using the probabilities derived from the calibration samples. In the case of homozygous contributors, dropout and stutter are simulated for both the alleles in the contributor. Two assumptions are made with regard to dropout and stutter:
1. Dropout and stutter of one allele of a contributor are assumed to be independent of dropout and stutter of the contributor's other allele.
2. Dropout and stutter of an allele from a contributor are assumed to be independent of dropout and stutter of the same allele from another contributor.

Once the alleles that have dropped out and the alleles that given rise to stutter have been established, $Pr(E_i|G=g, \Theta=\theta, N=n)$ is computed for each sample based on the distribution assumption, for example Gaussian distribution, using the means and standard deviations for the different types of peaks from the calibration samples. After a large number of samples, all the computed values of $Pr(E_i|G=g, \Theta=\theta, N=n)$ are averaged to obtain an approximation of (1). The APP is then calculated according to the following formula:

$$Pr(N=n|E) = \frac{Pr(E|N=n)}{\sum_{n=1}^{n_{max}} Pr(E|N=n)}.$$

EXAMPLES

Example 1: Generation of Calibration Samples

To generate the calibration samples, high molecular weight DNA was extracted from 35 single source samples using standard organic extraction procedures. The samples were whole blood, dried blood stains or saliva. The blood stains were either on Whatman® paper or cloth swatches. Saliva samples were either whole saliva or dried buccal swabs on cotton. Briefly, the organic extraction consisted of incubating the sample in 300 µg/mL of Proteinase K and 2% v/v SDS (sodium dodecyl sulfate) solution at 37° C. for 2 hours to overnight. Purification was accomplished with phenol/chloroform and alcohol precipitation. The DNA was dissolved in 50 µl of TE buffer (10 mM Tris, 0.1 mM EDTA, pH 8.0) at 56° C. for 1 hour. Absolute DNA quantification was performed using real-time PCR and the Quantifiler® Duo™ Quantification kit according to the manufacturer's recommended protocol and one external calibration curve. A 7500 Sequence Detection System (Life Technologies, Inc.) was used for Ct (cycle threshold) detection. The extracted DNA was amplified using the manufacturer's recommended protocol (29 cycles) for AmpFlSTR® Identifiler® Plus Amplification Kit (Life Technologies, Inc). Single source samples were amplified using 0.25, 0.125, 0.063, 0.047, 0.031, 0.016 and 0.008 ng of DNA. The PCR reaction consisted of 15 µL of master mix, the calculated volume of template DNA based on target mass required, and enough Tris-EDTA (TE) buffer (10 mM at pH 8.0) to bring the total reaction volume to 25 µL. Amplification was performed on Applied Biosystems' GeneAmp® PCR System 9700 using 9600 emulation mode. Positive and negative amplification controls were also run and showed expected results. Fragment separation was accomplished by using a 3130 Genetic Analyzer (Life Technologies, Inc.) and a mixture containing appropriate amounts of HiDi (highly-deionized) formamide (8.7 µl/sample) (Life Technologies, Inc.) and GeneScan™-600 LIZ™ Size Standard (0.3 µL/sample) (Life Technologies, Inc.). A volume of 9 µL of that mixture and 1 µL of sample, negative or ladder was added to the appropriate wells. The samples were incubated at 95° C. for 3 minutes and snap-cooled at −20° C. for 3 minutes. Five, ten, and twenty second injections at 3 kV were performed on each of the samples and run according to the manufacturer's recommended protocol. Fragment analysis was performed using GeneMapper IDX v1.1.1 (Life Technologies, Inc.) using Local Southern sizing and an RFU threshold of 1. A threshold of 1 RFU was used in order to capture all peak height information, i.e. the allelic peaks, baseline noise and stutter peaks, in the signal. Known artifacts such as pull-up, spikes, −A, and artifacts due to dye dissociation were manually removed. A peak was considered pull-up if it was the same size (+/−0.3 bp) as a larger peak in another color and below 5% of the height of the larger peak. Peaks were determined to be 'spikes' if they were in greater than 2 colors and in the same position. Peaks were considered to be −A if they were one base pair smaller than an allele and peaks determined to originate from dye dissociation had to be in the same position, in the same color channel and be observed in multiple samples. The Genotypes Table, which included the File Name, Marker, Dye, Allele, Size and Height, was exported.

Example 2: 1,2,3,4,5-Person Experimental Samples

Methods

1-, 2-, 3-, 4- and 5-person experimental samples were used for testing, FIG. 5, referred to as Testing Set 1. These 1-person samples were created using the same protocol described for the samples in the calibration set. The mixtures were created by mixing appropriate volumes of the single source DNA extracts to attain the various ratios specified in the following table:

TABLE 1

The Mixture Ratios Used to Create Samples in Testing Set 1

| Number of Contributors | Mixture ratios used |
|---|---|
| 2 | 1:1, 1:2, 1:4, 1:9, 1:19 |
| 3 | 1:1:1, 1:2:1, 1:4:1, 1:9:1, 1:2:2, 1:4:4, 1:9:9 |
| 4 | 1:1:1:1, 1:1:2:1, 1:1:4:1, 1:1:9:1, 1:2:2:1, 1:4:4:1, 1:9:9:1 |
| 5 | 1:1:1:1:1, 1:1:2:1:1, 1:1:4:1:1, 1:1:9:1:1, 1:1:2:2:1, 1:1:4:2:1, 1:2:2:2:1, 1:4:4:4:1 |

Once mixed, these samples were re-quantified and then amplified using the same target masses used for the single-source samples. In the case of mixtures, the samples were created using various kinds of mixture ratios in such a way that each individual contributed at least two cells' worth of DNA, which corresponds to approximately 0.013 ng of DNA. None of the contributors to the Calibration Set were present in Testing Set 1 and none of the contributors to Testing Set 1 were present in the Calibration Set.

The contributors to Testing Set 1 were US Caucasian, Hispanic, Asian or Black. Samples were not blocked together based on their population into one mixture in order To mimic evidentiary items. The allele frequencies used was that of the US Caucasian population. Four alleles belonging to five contributors in the calibration samples were not present in the frequency table. These four alleles were added to the frequency table, each with a frequency of 5/2N (corresponding to a value of 0.7%), where N is the number of individuals sampled from, as suggested by the National Research Council (NRC-II 1996).

In Testing Set 1, the 1-person samples contained DNA from 20 different individuals, the 2-person samples contained DNA from 4 different individuals (2 combinations), the 3-person samples contained DNA from 3 different individuals (1 combination), the 4-person samples contained DNA from 4 different individuals (1 combination) and the 5-person samples contained DNA from 5 different individuals (1 combination). The set of contributors was re-used but each sample was unique because variation was introduced through a) using different total DNA masses and b) using different mixture ratios. Thus, the amount of DNA from each contributor varied across the samples.

To test the performance of the methods when subjected to diverse scenarios of allele-sharing, a set of 40 simulated mixtures was created using various genotype combinations, total DNA input and mixture ratios according to the following table:

TABLE 2

Number of Simulated Mixtures Used in Testing Set 2

| Mixture Type | Number of Samples | DNA Amounts (ng) | Mixture Ratios |
|---|---|---|---|
| 2-person | 8 | 0.08, 0.11, 0.12, 0.14, 0.17, 0.19 | 1:1, 1:2, 1:3, 1:4, 1:8 |
| 3-person | 10 | 0.09, 0.12, 0.14, 0.17, 0.20, 0.23, 0.25 | 1:1:1, 1:1:2, 1:1:3, 1:2:2, 1:2:3, 1:2:4, 1:3:4, 1:4:4, 1:4:8 |
| 4-person | 12 | 0.11, 0.16, 0.17, 0.19, 0.20, 0.23, 0.25, 0.26 | 1:1:1:8, 1:1:2:3, 1:2:2:2, 1:2:2:4, 1:2:3:4, 1:2:4:4, 1:2:4:8, 1:3:4:4, 1:3:4:8, 1:4:4:8 |
| 5-person | 10 | 0.22, 0.25, 0.28, 0.29 | 1:1:1:8:8, 1:1:2:2:2, 1:1:4:4:8, 1:2:2:2:2, 1:2:3:4:4, 1:2:3:4:8 |

The mixtures were simulated by adding the signal from the 1-person samples in Testing Set 1 at the 10 s injection time in various combinations. The samples were simulated in such a way that no combination of contributors was repeated. Thus, the eight 2-person samples had eight combinations; the ten 3-person samples had ten combinations and so on.

An important thing to note is that the systems and methods herein are meant to assist the analyst in interpreting the DNA profile, and not to be used as a standalone tool to pick the number of contributors with the highest probability. The usefulness stems from the fact that for complex mixtures that are hard to analyze, it can identify the range in which the number of contributors is most likely to lie. MLE, like the current systems and methods, also gives a probability distribution on the number of contributors. Hence while analyzing the performance of these two methods, two different ways for assessing their accuracy were developed. One was to term the result as 'accurate' if the number of contributors in the sample had the highest probability (Maximum probability). The other method defined an accurate result as one in which the number of contributors in the sample had a probability of at least 1% (1% probability). The logic behind this is that if a number has a probability of at least 1% then it is quite likely to be the actual underlying number of contributors and therefore cannot be ignored during subsequent steps of the mixture interpretation process. Thus, more than one number of contributors might have to be considered for mixture interpretation if they all have a probability of at least 1%. The accuracy was tested on Testing Set 1 using a higher threshold of 10% and found the results to be similar to the ones obtained using a 1% threshold, see table below:

TABLE 3

Accuracy on Testing Set 1 using 1% and 10% Probability Threshold

| Number of Contributors | Number of Samples | 1% Probability Correct Answers | 10% Probability Correct Answers |
|---|---|---|---|
| 1 | 60 | 58 | 58 |
| 2 | 89 | 88 | 88 |
| 3 | 48 | 48 | 44 |
| 4 | 39 | 34 | 30 |
| 5 | 42 | 39 | 39 |

The programs were written in the Java programming language. It takes on average 10 hours to compute the APP on the number of contributors to a sample on a quad core system with 2 GHz of processor speed with the maximum possible number of contributors n_"max"=5. To reduce computational running time, the probabilities for all n up to 5 for all samples were not computed. Our results suggest that the distribution from the methods was unimodal—having a single peak and then decreasing in value. Hence while computing the APP distribution, if the APP for n_0 is less than one-thousandth of the APP for n_0−1, the calculation was stopped at n_0, assuming that the APP for n>n_0 is negligible.

The performance was compared with the MAC and the MLE methods. MAC uses the number of peaks observed in the signal to determine the number of contributors while MLE uses the number of peaks as well as the frequencies of the alleles in the signal. Both methods depend upon the establishment of a threshold to determine the set of true peaks. The threshold is typically chosen by a laboratory based on validation data. The current system and methods on the other hand, does not depend upon the setting of a threshold and works on the entire electropherogram obtained. Two types of thresholds were used for MAC and MLE for comparison purposes: a constant threshold of 50 RFU at all loci, and a variable threshold set as the height of the highest noise peak observed in the calibration data per dye color per DNA amount per time of injection. The average of the variable thresholds was 19, 33 and 52 RFU for the 5, 10 and 20 s injection samples respectively. Application of MAC and MLE also uses a stutter threshold to filter out the peaks in the n−4 position of peaks above the threshold. The stutter filter recommended by the manufacturer was used at each locus to filter out the stutter peaks. MAC and MLE was implemented using the Python programming language.

Results

Figure 6:
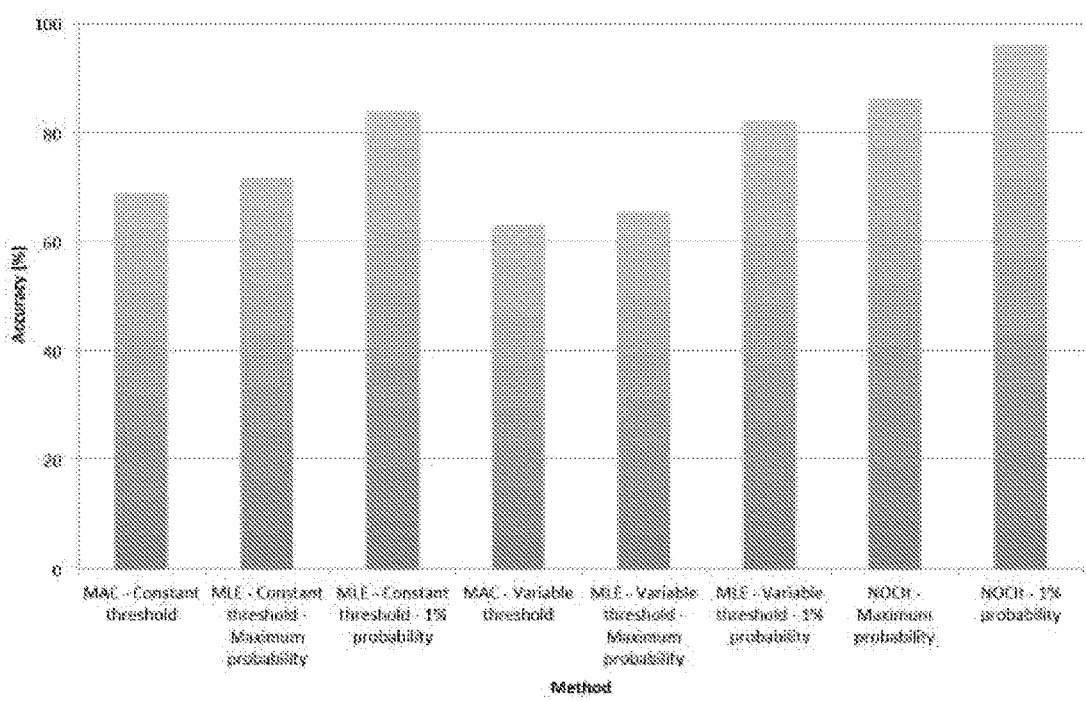
FIG. 6 is the accuracy of the three methods used in the study across all the samples in Testing Set 1 in Example 1.

Across all samples in Testing Set 1, the maximum probability form of MLE (constant threshold accuracy: 72%, variable threshold accuracy: 65%) had a higher accuracy than MAC (constant threshold accuracy: 69%, variable threshold accuracy: 63%) with both the constant and the variable thresholds (FIG. 6). Both MAC and MLE had a higher accuracy with the constant threshold of 50 RFU compared to the variable threshold. While using the 1% probability form as well, MLE had a higher accuracy than MAC with both the constant (accuracy: 84%) and the variable (accuracy: 82%) thresholds. Across all samples, applied using the maximum probability and the 1% probability forms, this current method had a higher accuracy than MAC and MLE. Like MLE, the current 1% probability form (96%) had a higher accuracy than the maximum probability form (86%).

Figure 7:
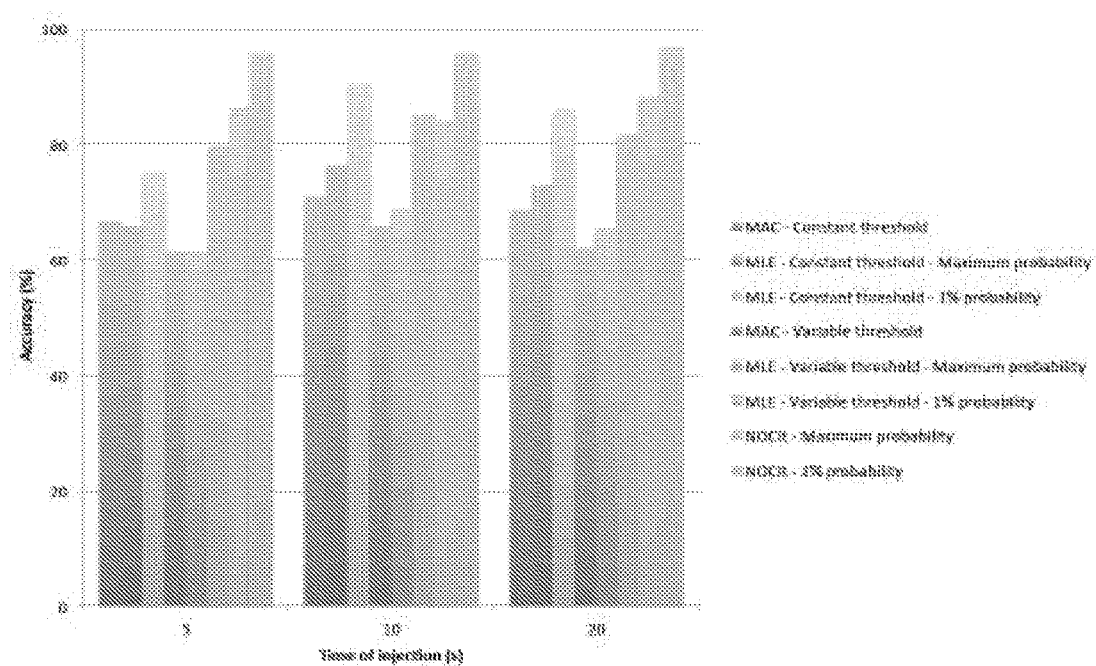
FIG. 7 is the results of the performance of the three methods on Testing Set 1 according to the time of injection used while injecting the sample into the capillary.

The results of the performance of the three methods on Testing Set 1 at the three times of injection are provided in FIG. 7. Changing the injection time did not have an impact on the performance of the three methods. The 1% probability form was found to have the highest accuracy at all three injection times.

Figure 8:
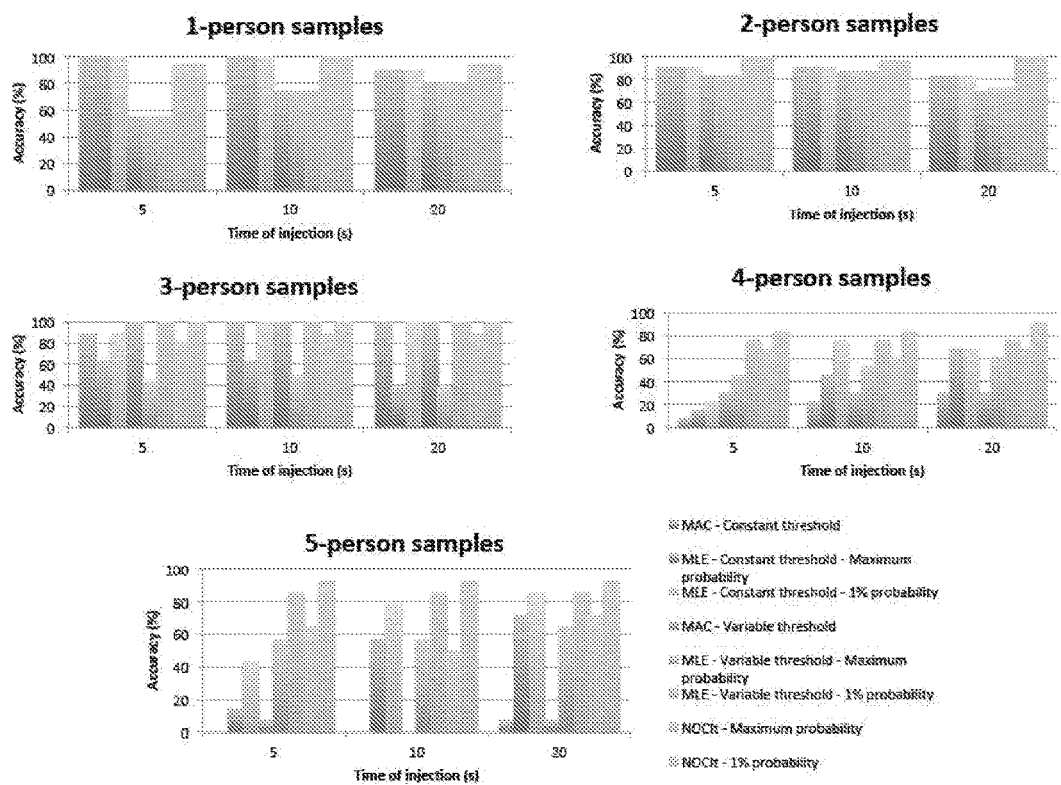
FIG. 8 shows that the performance of the methods on Testing Set 1 as the number of contributors to the sample is increased.
Figure 9:
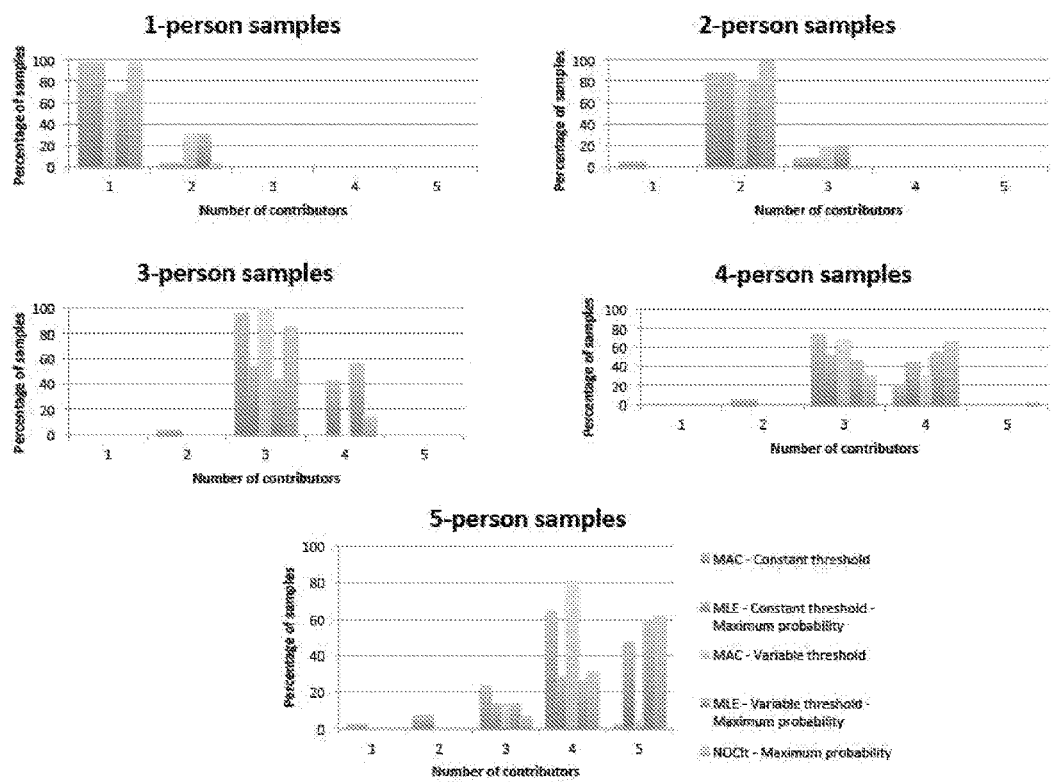
FIG. 9 is the percentage of calls made for each number of contributors (from 1-5) by the 3 methods for the samples in Testing Set 1.

FIG. 8 and FIG. 9 show how the performance of the methods changes as the number of contributors to the sample is increased. The accuracy of MAC and MLE were comparable for the 1-, 2- and 3-person samples, while the accuracy of MLE was higher than MAC for the more complex 4- and 5-person samples (FIG. 8). As expected, MAC and MLE gave underestimates for mixtures with more than one contributor, due to sharing of alleles between the contributors. Overestimates were observed for both MAC and MLE for the 1- and 2-person samples, due to stutter peaks having a higher than expected height at one or more loci. MLE, unlike MAC, also resulted in overestimates for the 3-person samples (FIG. 9).

The accuracy of the 1% probability method was 87% or higher for the 1-, 2- 3-, 4- and 5-person samples (FIG. 8). The maximum probability form had an accuracy that was close to the 1% probability form for the 1- and 2-person samples. The larger difference between the accuracy of the two forms for the 3-, 4- and 5-person mixtures indicates that in the instances in which the systems and methods do not come up with the highest probability for the actual number of contributors, it still successfully identifies the range in which the number is most likely to lie, even for complex mixtures.

There were underestimates with the 4- and 5-person samples. These underestimated samples were characterized by high levels of dropout at multiple loci. There were three cases in which a 5-person sample was called as a 3-person sample. Apart from that, the underestimated samples were called as one less than the actual number of contributors. For the 1-, 2-, 3- and 4-person samples in the number of contributors were overestimated, the number of contributors was calculated as one more than the actual number (FIG. 9). These samples were found to contain elevated levels of reverse and/or forward stutter at one or more loci.

Figure 10:
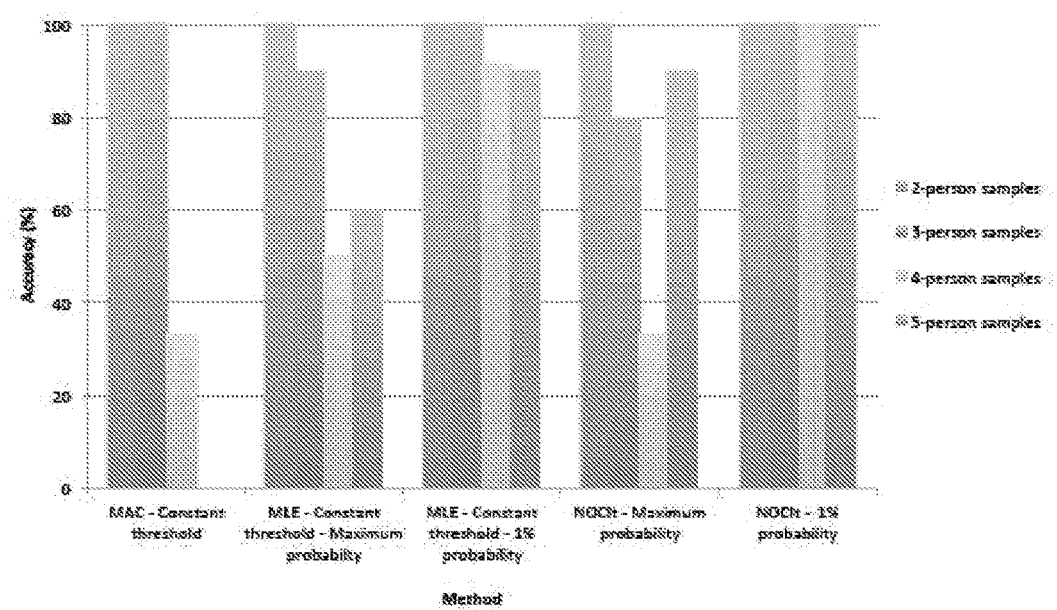
FIG. 10 shows the performance of the three methods on the artificially created samples in Testing Set 2.

FIG. 10 shows the performance of the 3 methods on the simulated profiles in Testing Set 2. MAC and MLE were tested using only the constant threshold of 50 RFU. The 1% probability form of the present invention had an accuracy of 100%, while the 1% probability form of MLE had an accuracy of 95%. With regards to their maximum probability forms, both the present systems and methods and MLE had an accuracy of 73%. The accuracy of MAC was 55% with the samples in Testing Set 2.

On the experimental samples used for testing, both the maximum probability and the 1% probability forms had a higher accuracy than the MAC and MLE methods using either a constant threshold of 50 RFU or a variable threshold based on the height of the noise peaks in the calibration data set. Similar results were obtained when the accuracy was compared at the three injection times used. These results indicate that using the quantitative data in the signal, in addition to the qualitative data, results in a better estimate when determining the number of contributors.

In addition to the experimental samples used, the three methods were also tested on 40 simulated mixtures containing between 2 and 5 contributors created by adding the signal from the experimental 1-person samples at the 10 s injection time in various combinations. The 1% probability form had an accuracy of 100% on the simulated mixtures, performing better than the best available method in identifying the number of contributors Our results suggest that the application of an analytical threshold, and the resulting loss of information about the peaks that do not cross the threshold, is generally detrimental to mixture interpretation when dealing with low template samples. In the case of low template samples, there is a chance that usage of a threshold could lead to dropout of alleles that might otherwise have been observed.

Applying a stutter filter to filter out the stutter peaks might not work all the time, due to stutter peaks having higher than expected peak heights. This was found to be the cause of the overestimates from the MAC and MLE methods.

All three methods used in this study were not affected by changes in the time of injection. Using a constant threshold of 50 RFU resulted in an accuracy higher than the accuracy with a variable threshold based on the height of the noise peaks in the calibration set for both MAC and MLE.

Overall, both MLE and the present systems and methods had a higher accuracy with the 1% probability form compared to the maximum probability form, indicating the utility of both the methods in identifying the range in which the number of contributors is likely to lie, even if they do not come up with the highest probability for the actual number of contributors. This can be a very useful piece of information when analysing samples with low DNA input and/or samples with a large number of contributors.

The accuracy of MLE and MAC were similar to each other, with MLE having a slightly higher accuracy, when the maximum probability form was used for MLE. Using the 1% probability form of MLE resulted in a bigger difference in the accuracy of the two methods.

The accuracy of MAC was similar to that of MLE for the 1-, 2- and 3-person samples. For the more complex 4- and 5-person mixtures, the accuracy of MLE was higher than that of MAC. As expected, MAC gave underestimates for samples with more than 1 contributor. MAC also had overestimates for some of the 1- and 2-person samples, when the stutter ratio was higher than the expected level. While it is true that MAC gives the minimum number of contributors when the signal-to-noise ratio is sufficiently high, samples that contain elevated stutter could result in an overestimate. The results from MLE were similar to MAC, with underestimates for samples with more than 1 contributor and overestimates for some of the 1-, 2- and 3-person samples.

The underestimates were characterized by high levels of dropout at multiple loci and were called as one less than the actual number of contributors (apart from three cases in which 5-person samples were called as 3-person samples), while the overestimates were called as one more than the actual number of contributors and were found to contain elevated levels of reverse and/or forward stutter at one or more loci.

The APP tended to support one number of contributors much more than the others. The average of the highest APP across all samples tested was 0.92. The average of the second highest APP across all the samples was 0.07. The third and subsequent highest APP had negligibly low values. Thus, though a 1% was chosen threshold for our main results, using a 10% threshold resulted in similar accuracy.

Example 3: 1,2,3-Person Experimental Studies

The performance of the disclosed method and system is tested on 1 person (the calibration source), 2 person and 3 person mixtures. MAC and MLE were also run on the same set of samples for comparison purposes. The following table shows the number of samples used at the different DNA amounts for each time of injection:

TABLE 4

Total Number of Samples, 1,2,3-Person Experimental Studies

| | Number of Contributors | | | | | | | | |
|---|---|---|---|---|---|---|---|---|---|
| | 1 Injection Times | | | 2 Injection Times | | | 3 Injection Times | | |
| DNA Amount (ng) | 5 | 10 | 20 | 5 | 10 | 20 | 5 | 10 | 20 |
| 0.007 | 74 | 95 | 74 | 5 | 5 | 5 | 7 | 7 | 7 |
| 0.016 | 72 | 95 | 74 | 5 | 5 | 5 | 7 | 7 | 7 |
| 0.031 | 72 | 89 | 74 | 5 | 5 | 5 | 7 | 7 | 7 |
| 0.047 | 73 | 74 | 73 | 5 | 5 | 5 | 7 | 7 | 7 |
| 0.062 | 74 | 92 | 75 | 5 | 5 | 5 | 7 | 7 | 7 |
| 0.125 | 73 | 92 | 72 | 5 | 5 | 5 | 7 | 7 | 7 |
| 0.250 | 74 | 95 | 74 | 5 | 5 | 5 | 7 | 7 | 7 |
| Total | 512 | 632 | 516 | 35 | 35 | 35 | 49 | 49 | 49 |
| | | 1660 | | | 105 | | | 147 | |

MAC and MLE were evaluated using a threshold of 50 RFU, the most commonly used threshold. Overall the disclosed method and system exhibits a higher accuracy rate (95%) compared to both MAC (84%) and MLE (53%) across all samples tested.

Example 4: Other Experimental Studies

In an example, the disclosed method and system exhibits a 98% accuracy rate on one (1) person samples. The accuracy rate is 99% for 5 s and 10 s injection time samples, but may be lower 20 s samples, where the overestimates increase. MAC, in contrast, has an accuracy of 87% across all times of injection for the 1-person samples. The accuracy rate may decreases with increase in time of injection, as the number of overestimates increase. There are a few underestimates by MAC at the lower DNA amounts at the 5 s and 10 s injection samples.

However there are no underestimates at the 20 s injection samples. The number of overestimates from MAC increases with DNA amount at all 3 times of injection. MLE has an overall accuracy of only 52% for the 1-person samples. This is due to the fact that in this comparison MLE was set to depend upon every locus having the number of alleles in the range of 1 to 2n, where 'n' is the number of contributors. Hence it fails to identify the correct number of contributors in cases where there is allele or locus dropout. At all 3 injection times, as the signal to noise ratio increases with the DNA amount, so does the accuracy of MLE.

In an example experiment, the disclosed method and system exhibits an accuracy of 84% for the two (2) person samples. The accuracy rate increases as the time of injection increases. The only instances where underestimates dominate the analysis, at all 3 injection times, are for lower DNA amounts of 0.007 ng and 0.01 ng. At the higher DNA amounts (0.03 ng and above) it has a 100% accuracy rate at all 3 times of injection. MAC has an accuracy of 69% for the 2 person samples. Its accuracy improves from 57% for the 5 s samples to 77% for the 10 s samples and then decreases to 74% for the 20 s samples. For the 5 s and 10 s samples, the accuracy increases with DNA amount as underestimates occur only at the lower DNA amounts.

For the 20 s samples, accuracy increases with DNA amount, then decreases as overestimates occur at the higher DNA amounts. MLE has an accuracy rate of 61% for 2 person samples, with accuracy again increasing with injection time. Similar to MAC, for the 5 s and 10 s samples, the accuracy increases with DNA amount as underestimates occur only at the lower DNA amounts. For the 20 s samples, accuracy increases with DNA amount, then decreases as overestimates occur at the higher DNA amounts.

In an example experiment, the disclosed method and system exhibits an overall accuracy of 64% for three (3) person samples. The accuracy of the disclosed method and system increases from 61% for the 5 s samples to 67% for the 10 s and 20 s samples. At all injection times, the disclosed method and system gives underestimates only at the lower DNA amounts (0.007 ng to 0.047 ng). At 0.06 ng and above, it has a 100% accuracy rate. MAC and MLE both have an identical accuracy rate of 55%, with performance improving with time of injection and DNA amount at all 3 times of injection.

CONCLUSION

The current invention has been designed in such a way that forensic laboratories can analyze an unknown sample using the frequencies of alleles in the population that they are interested in. Laboratories need to generate the calibration samples, consisting of single source samples with known genotypes. The calibration samples need to be created using a dilution series and amplified from a range of DNA masses. The profile of the unknown sample to be analyzed should be created using the same protocol used for the calibration samples. Areas for future work include testing it on mixtures with related contributors, samples obtained from touched items and samples with contributors from a population that is different from the one used for allele frequency data.

Although the invention has been described and illustrated in the foregoing illustrative embodiments, it is understood that the present disclosure has been made only by way of example, and that numerous changes in the details of implementation of the invention can be made without departing from the spirit and scope of the invention, which is limited only by the claims which follow. Features of the disclosed embodiments can be combined and rearranged in various ways.

What is claimed is:
1. A method for determining a number of contributors to a DNA mixture, the method comprising:
   analyzing each of a plurality of calibration samples at a plurality of concentrations to generate a calibration sample profile corresponding to each of the plurality of calibration samples wherein each calibration sample profile comprises a plurality of allele peaks, and wherein each of the calibration samples is a biological sample comprising DNA that is obtained from a single contributor;
   generating, by a processor, for each of the plurality of calibration samples, calibration data from the corresponding calibration sample profile by modeling heights of the plurality of allele peaks, wherein the calibration data models one or more variables as a function of input DNA mass in the corresponding calibration sample;
   analyzing a test sample to generate a test sample profile, wherein the test sample is a biological sample com- prising a DNA mixture from one or more contributors, and wherein the number of contributors is unknown;

analyzing, by the processor, the calibration data and the test sample profile to generate a probability distribution of a number of contributors to the test sample for estimating the number of contributors to the DNA sample; and using the estimated number of contributors to determine whether an individual should be included as a contributor to the DNA mixture during forensic analysis, wherein:

the plurality of calibration sample and the test sample are analyzed using the same laboratory device under the same test conditions.

2. The method of claim 1, wherein generating, for each of the plurality of calibration samples, calibration data from the corresponding calibration sample profile by modeling heights of the plurality of allele peaks further comprises:

identifying a type for each of the plurality of allele peaks in the calibration sample profile as at least one of the following types: a true peak, a reverse stutter peak, a forward stutter peak, or a noise peak; and for each allele peak type:
generating a Gaussian distribution, and
identifying a mean and a standard deviation for each of plurality of loci.

3. The method of claim 2, further comprising, for each of the plurality of loci, determining a dropout rate and a rate of occurrence of stutter.

4. The method of claim 2, wherein analyzing the calibration data and the test sample profile to generate the probability distribution of the number of contributors to the test sample comprises using means and standard deviations for the allele peak types in the calibration data to generate the probability distribution function.

5. The method of claim 1, wherein analyzing the calibration data and the test sample profile to generate the probability distribution of the number of contributors to the test sample comprises using a Monte Carlo sampling algorithm to generate the probability distribution.

6. The method of claim 1, further comprising determining the number of contributors to the test sample as a number of contributors with the highest probability on the probability distribution.

7. The method of claim 1, further comprising determining the number of contributors to the test sample as a range on the probability distribution within which the number of contributors is most likely to lie.

8. The method of claim 1, wherein the one or more variables are selected from at least one of the following: a baseline peak height, drop out, stutter, and presence of one or more artifacts.

9. The method of claim 1, further comprising:
determining an amount of DNA in the test sample; and
using the amount to generate the probability distribution.

10. The method of claim 1, wherein the plurality of calibration samples include a plurality of biological samples comprising DNA material from the same person but at different levels of DNA concentration.

11. The method of claim 1, wherein the DNA mixture is derived from a biological sample evidence collected at a crime scene and the estimated number of contributors is used to assess the weight of the biological sample evidence.

12. A system for determining a number of contributors to a DNA mixture, the system comprising:
a laboratory device configured to perform measurements under a set of test conditions;
a processing device; and
a non-transitory computer readable medium comprising one or more programming instructions which when executed by the processing device, cause the processing device to:

receive, from the laboratory device, a plurality of calibration profiles corresponding to a plurality of calibration samples, wherein each of the plurality of calibration profiles comprises a plurality of allele peaks and is generated by the laboratory device by analyzing corresponding calibration sample at a plurality of concentrations under the set of test conditions, and wherein each of the calibration samples is a biological sample comprising DNA that is obtained from a single contributor, generate, for each of the plurality of calibration samples, calibration data from the corresponding calibration sample profile by modeling heights of the plurality of allele peaks, wherein the calibration data models one or more variables as a function of input DNA mass in the corresponding calibration sample, receive, from the laboratory device, a test sample profile generated by analyzing the test sample under the set of test conditions, wherein the test sample is a biological sample comprising a DNA mixture from one or more contributors and wherein the number of contributors is unknown, analyze the calibration data and the test sample profile to generate a probability distribution of a number of contributors to the test sample for estimating the number of contributors to the DNA sample; and using the estimated number of contributors to determine whether an individual should be included as a contributor to the DNA mixture during forensic analysis.

13. The system of claim 12, wherein the one or more programming instructions that cause the processing device to generate, for each of the plurality of calibration samples, calibration data from the corresponding calibration sample profile by modeling heights of the plurality of allele peaks further comprise one or more instructions that cause the processing device to:

identify a type for each of the plurality of allele peaks in the calibration sample profile as at least one of the following types: a true peak, a reverse stutter peak, a forward stutter peak, or a noise peak; and for each allele peak type:
generate a Gaussian distribution, and
identify a mean and a standard deviation for each of plurality of loci.

14. The system of claim 13, further comprising one or more instructions that cause the processing device to, for each of the plurality of loci, determine a dropout rate and a rate of occurrence of stutter.

15. The system of claim 13, wherein the one or more programming instructions that cause the processing device to analyze the calibration data and the test sample profile to generate the probability distribution of the number of contributors to the test sample further comprise one or more instructions that cause the processing device to use means and standard deviations for the allele peak types in the calibration data to generate the probability distribution function.

16. The system of claim 12, wherein the one or more programming instructions that cause the processing device to analyze the calibration data and the test sample profile to generate the probability distribution of the number of contributors to the test sample further comprise one or more instructions that cause the processing device to use a Monte Carlo sampling algorithm to generate the probability distribution.

17. The system of claim 12, further comprising one or more instructions that cause the processing device to determine the number of contributors to the test sample as a number of contributors with the highest probability on the probability distribution.

18. The system of claim 12, further comprising one or more instructions that cause the processing device to determine the number of contributors to the test sample as a range on the probability distribution within which the number of contributors is most likely to lie.

19. The system of claim 12, wherein the one or more variables are selected from at least one of the following: a baseline peak height, drop out, stutter, and presence of one or more artifacts.

20. The system of claim 12, further comprising one or more instructions that cause the processing device to:
   determine an amount of DNA in the test sample; and
   use the amount to generate the probability distribution.

21. The system of claim 12, wherein the plurality of calibration samples include a plurality of biological samples comprising DNA material from the same person but at different levels of DNA concentration.

\* \* \* \* \*